(12) United States Patent
Ueno et al.

(10) Patent No.: US 7,151,194 B2
(45) Date of Patent: Dec. 19, 2006

(54) METHOD FOR PRODUCTION OF ACRYLIC ACID

(75) Inventors: Kouji Ueno, Himeji (JP); Harunori Hirao, Himeji (JP); Naoki Serata, Himeji (JP); Takeshi Yokogoshiya, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/859,025

(22) Filed: Jun. 2, 2004

(65) Prior Publication Data

US 2004/0249201 A1 Dec. 9, 2004

(30) Foreign Application Priority Data

Jun. 5, 2003 (JP) ............................. 2003-160772

(51) Int. Cl.
*C07C 51/16* (2006.01)
*C07C 51/42* (2006.01)

(52) U.S. Cl. ....................... 562/545; 562/600
(58) Field of Classification Search ................ 562/600, 562/521, 532, 542, 545
See application file for complete search history.

(56) References Cited

U.S. PATENT DOCUMENTS

| | | | |
|---|---|---|---|
| 5,315,037 A | 5/1994 | Sakamoto et al. | 562/600 |
| 5,817,865 A | 10/1998 | Machhammer et al. | 560/208 |
| 6,482,981 B1 | 11/2002 | Ueno et al. | 562/600 |

FOREIGN PATENT DOCUMENTS

EP 1 059 281 5/2000

*Primary Examiner*—Taylor Victor Oh
(74) *Attorney, Agent, or Firm*—Mathews, Shepherd, McKay & Bruneau, P.A.

(57) ABSTRACT

A method for producing acrylic acid from an acrylic acid-containing solution of high concentration without performing azeotropic distillation is provided. This method of producing acrylic acid comprises steps of absorbing acrylic acid-containing gas, distilling the acrylic acid-containing solution without using an azeotropic solvent thereby obtaining crude acrylic acid as a column bottom stream and/or a column side stream, and supplying the crude acrylic acid to a crystallizing step and melt crystallizing the crude acrylic acid thereby obtaining purified acrylic acid.

12 Claims, 1 Drawing Sheet

FIGURE

METHOD FOR PRODUCTION OF ACRYLIC ACID

BACKGROUND OF THE INVENTION

1. Field of the Invention

This invention relates to a method for producing acrylic acid by distilling an acrylic acid-containing solution without using an azeotropic solvent, obtaining crude acrylic acid as a column bottom stream and/or a column side stream of a distillation column, and then crystallizing the crude acrylic acid.

2. Description of the Related Art

Commercial production of acrylic acid generally resorts to the method of propylene oxidation which consists in subjecting propylene and/or acrolein to catalytic gas phase oxidation. When acrylic acid is produced by this method of propylene oxidation, the step of propylene oxidation gives rise to such impurities as water, acids like propionic acid, acetic acid, and maleic acid, and aldehydes like acetone, acrolein, furfural, and formaldehyde in the form of by-products. The gas containing these by-products is absorbed as an acrylic acid-containing solution generally via contact with an absorbent and obtained the solution is subsequently separated the absorbent by distillation etc.

One known method, for example, produces acrylic acid of high purity by absorbing an acrylic acid-containing gas resulting from catalytic gas phase oxidation with a high boiling solvent, distilling the acrylic acid-containing solution thereby separating it into the solvent and crude acrylic acid, and subsequently subjecting the crude acrylic acid to a process of crystallization (JP-A-1997-227445). This method comprises carrying out a step of absorption of an acrylic acid-containing gas after the gas has been cooled with a venturi, carrying out a step of removing a low boiling compound subsequent to the step of absorption, thereafter separating the acrylic acid-containing solution in a distillation column into a high boiling substance and a low boiling substance, withdrawing crude acrylic acid as a liquid via the intermediary stage of the column, and purifying the crude acrylic acid by a step of crystallization.

When an aqueous solution can be used as an absorbent for acrylic acid in the place of an expensive high boiling solvent, the use of this aqueous solution proves economical. Particularly, when this aqueous solution is capable of absorbing the acrylic acid-containing solution in high concentration, the use of the aqueous solution is efficient in respect that it results in decreasing the amount of treatment at the subsequent steps of purification. A method has been disclosed which comprises introducing an acrylic acid-containing gas into an absorption column, absorbing with aqueous solution containing acetic acid thereby effecting absorption of acrylic acid therein, and producing as the bottom liquid of the absorption column an acrylic acid-containing solution composed of 50–80 wt % of acrylic acid, 2–5 wt % of acetic acid, and the balance of water (JP-A-1993-246941).

This method obtains purified acrylic acid by subjecting the acrylic acid-containing solution to azeotropic dehydration using a mixed solution of two or more azeotropic solvents and subsequently passing the product of dehydration through such steps as the removal of high boiling substance.

Still another method has been disclosed which, in the absorption with water of an acrylic acid-containing solution resulting from a reaction of catalytic gas phase oxidation, comprises supplying the recovery water emanating from the step of azeotropic dehydration to the absorption column, supplying the resultant acrylic acid-containing solution to a stripping column, and obtaining an acrylic acid solution composed of 70.9 wt. % of acrylic acid, 25.6 wt. % of water, and 2.0 wt. % of acetic acid via the bottom of the stripping column (JP-A-2001-199931). This method obtains purified acrylic acid by performing azeotropic dehydration of the acrylic acid-containing solution and subsequently subjecting the product of dehydration to the step of crystallization.

For the purpose of obtaining crude acrylic acid substantially destitute of water by treating an aqueous acrylic acid solution by distillation, it is common to perform azeotropic distillation using an azeotropic solvent. The azeotropic distillation necessitates a step of solvent separation in order to reuse the azeotropic solvent. In JP-A-1993-246941 and JP-A-2001-199931 which disclose inventions involving use of an aqueous type absorbing solvent mentioned above, azeotropic dehydration using an azeotropic solvent is described. Thus, the development of a method which produces acrylic acid without a step of azeotropic distillation has been yearned for enthusiastically.

An attempt to obtain crude acrylic acid substantially destitute of water without performing azeotropic distillation results in causing acrylic acid to distill in a considerable amount from the top of the distillation column in consequence of azeotropy between acrylic acid and water, increasing the amount of acrylic acid expelled out of the system, and causing degradation of yield. Under these existing circumstances, the development of a method for producing acrylic acid in a high yield has been yearned for.

SUMMARY OF THE INVENTION

The present inventor has found that the step of production of acrylic acid is enabled to obviate the necessity for azeotropic distillation by using an acrylic acid-containing solution of high concentration, that when the acrylic acid-containing solution is withdrawn as a column side stream and a column bottom stream of the distillation column, obtained solution can be separated from a high boiling substance and a low boiling substance thereby obtaining crude acrylic acid, and that the crude acrylic acid can be purified by crystallization. Particularly by withdrawing the crude acrylic acid in a gaseous form in the distillation step prior to the crystallization, it is made possible to expel such high boiling substances as polymerization inhibitor and a substance causing coloration and obtain acrylic acid of high purity through several repetitions of crystallization. This invention has been perfected based on this knowledge.

By obtaining the crude acrylic acid from the acrylic acid-containing solution emanating from the distillation column of a column bottom stream and/or the column side stream and crystallizing the crude acrylic acid according to this invention, it is made possible to produce acrylic acid without performing the step of azeotropic dehydration.

This invention is particularly suitable for the purification of an acrylic acid-containing solution having a high acrylic acid concentration. The acrylic acid of such high concentration is attained with an effectively utilizing use of the recycle gas at the step of absorption and decrease the acrylic acid loss. Further, since the amount of acrylic acid contained in the recycle gas is decreased, the catalyst enjoys an increased service life. Moreover, the process is simplified and the productivity is exalted because the purification is carried out without the azeotropic dehydration. The invention will be described in detail below.

DESCRIPTION OF THE PREFERRED EMBODIMENT

Figure 1:
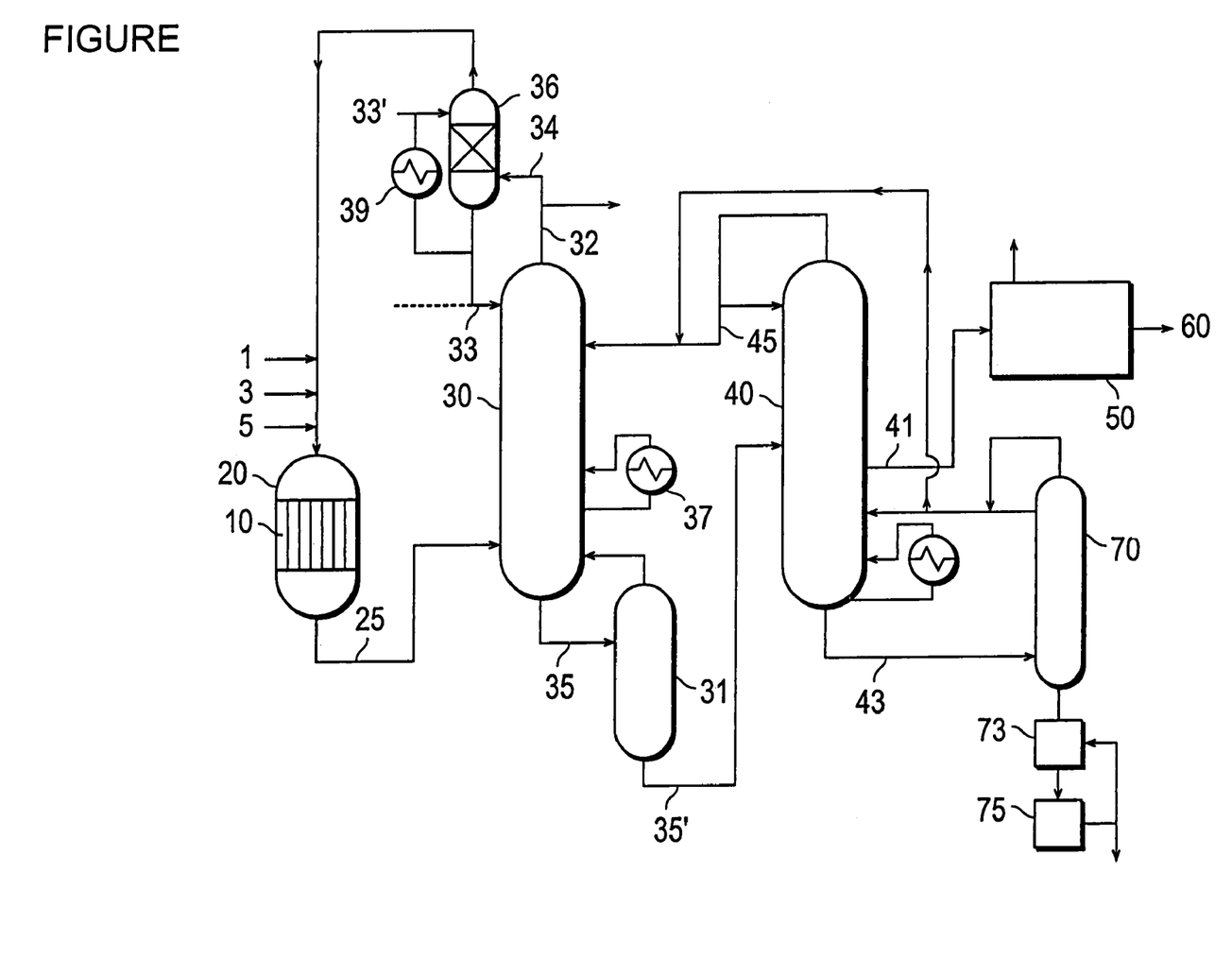
FIGURE is a process diagram illustrating one example of the preferred mode of embodying this invention.

The first aspect of this invention is directed toward providing a method for producing acrylic acid by a procedure comprising steps of a) introducing an acrylic acid-containing gas obtained by the reaction of catalytic gas phase oxidation of raw material of acrylic acid into an absorption column and brought into contact with an absorbing aqueous solution thereby obtaining an acrylic acid-containing solution, b) distilling the acrylic acid-containing solution without using an azeotropic solvent thereto thereby obtaining crude acrylic acid as a column bottom stream and/or a column side stream, and c) supplying the crude acrylic acid to a step of crystallization and melt crystallizing it thereby obtaining purified acrylic acid. The bottom liquid of the step of b) mentioned above may be supplied to a device for decomposing acrylic acid dimer so as to recover acrylic acid. Thus, the acrylic acid can be produced in a high yield. One example of the preferred mode of embodying this invention will be described below with reference to The FIGURE.

First, such a molecular oxygen-containing gas as air 3, such raw material 1 for acrylic acid as propylene and/or acrolein, and a diluting gas 5 are mixed. At this step, after the completion of the step of absorbing acrylic acid, a recycle gas 34 which is discharged via the top of the absorption column may be also mixed with air, propylene and/or acrolein, and diluting gas. The resultant mixed gas (hereinafter referred to occasionally as "raw material gas") is supplied to a reactor 20 packed with a catalyst 10 for catalytic gas phase oxidation and subjected to the reaction of catalytic gas phase oxidation so as to obtain an acrylic acid-containing gas 25. This gas 25 is supplied to the bottom of an absorption column 30 and an absorbing aqueous solution 33 is supplied via the top of the absorption column 30 and the acrylic acid-containing gas 25 and the absorbing aqueous solution 33 are brought into mutual contact. In this specification, the part of a discharged gas 32 via the top of the absorption column 30 which is circulated to the reactor will be referred to as "recycle gas" and the part thereof which is discarded to the out side of system will be referred to as "waste gas." In this invention, only the recycle gas 34 is introduced into a cooling column 36, cooled by gas-liquid contact with an absorbing water 33, newly supplied into the system and enabled induce condensation of a condensable substance contained in the recycle gas, and thereafter circulated to the reactor 20. The condensate so formed may be mixed with the absorbing water 33' mentioned above and supplied as the absorbing aqueous solution 33 to the absorption column 30. By adjusting the temperature of the top of the absorption column with a heat exchanger 37 disposed in the absorption column and cooling the recycle gas, it is made possible to obtain an acrylic acid-containing solution 35 containing acrylic acid of high concentration via the bottom of the absorption column.

The acrylic acid-containing solution 35 is supplied to an acrolein separation column 31, which separates the contained acrolein from the solution and delivers an acrylic acid-containing solution 35' having the acrolein content decreased via the bottom of the column. Incidentally, when the distillate from the top of the separation column 31 is circulated to the bottom of the absorption column 30, the acrylic acid distilled in conjunction with acrolein can be effectively recovered.

Then, the acrylic acid-containing solution 35' is supplied to the intermediate stage of a first distillation column 40 so as to remove the contained low boiling substance via the top of the column and then produce crude acrylic acid 41 substantially destitute of water as a column side stream. When the crude acrylic acid 41 is supplied to a crystallizing device 50, acrylic acid 60 is obtained as a finished product. The high boiling substance contained in bottom liquid 43 of the first distillation column 40 contains acrylic acid dimer. Thus, the bottom liquid 43 is supplied to a second distillation column 70 provided on the bottom thereof with a thin layer evaporator 73 so as to concentrate the acrylic acid dimer and then the dimer is retained in a dimer decomposing tank 75 so as to effect thermal decomposition of the dimer into acrylic acid. This acrylic acid is circulated via the second distillation column 70 to the first distillation column 40 so as to recover as a finished product.

This invention is characterized by effecting distillation of the acrylic acid-containing solution without addition of an azeotropic solvent thereto as described above. Advisably, therefore, the acrylic acid content of this solution exceeds 80 wt. %, preferably 85 wt. %, and particularly 87 wt. %. When the distillation is carried out in the absence of an azeotropic solvent while the acrylic acid content falls short of 80 wt. %, huge utilities are required for obtaining crude acrylic acid from the bottom and the side of the distillation column and the distillation column itself is inevitably required to be enlarged. This invention is aimed at providing a method for producing acrylic acid in a high yield with lowered acrylic acid loss without steps of azeotropic dehydration and solvent recovery.

In the present specification, the term "low boiling substance" refers to a substance having a lower boiling point than acrylic acid in the normal state and the term "high boiling substance" refers to a substance having a higher boiling point than acrylic acid in the normal state. The term "azeotropic solvent" refers to a solvent which forms an azeotropic mixture with water. The azeotropic solvents enumerated in JP-A-2001-19931 may be cited as concrete examples. The term "condensable substance" refers to a substance which is a liquid under the atmospheric pressure, the term "distillation" refers to a method which comprises heating a solution to the boiling point thereof and separating a volatile component contained therein, the term "stripping (in distillation)" refers to a method which comprises supplying a stripping gas and causing a target substance in a solution to pass into the gas phase, and the term "crystallization" refers to an operation of producing crystals from the liquid phase and the gas phase. Then, the term "step of dynamic crystallization" refers to a method of crystallization which induces movement of the liquid phase by forced convection caused with a pump etc. during crystallization and the term "step of static crystallization" refers to a method of crystallization which induces movement of the liquid phase exclusively by spontaneous convection requiring no pump. Now, this invention will be described in detail below.

(1) Step of Acrylic Acid Absorption

For the purpose of obtaining an acrylic acid-containing solution of high concentration, it is necessary either to decrease the amount of a water component introduced into the system or increase the amount of a water component discarded to the out side of system. For the purpose of minimizing the acrylic acid loss discarded to the out side of system, it is advisable to recycle the exhaust gas emanating via the top of the absorption column to the reactor. In this invention, by cooling the recycle gas thereby decreasing the amount of a water component forwarding the recycle gas to the reactor, it is made possible to decrease the amount of the water component introduced into the absorption column and obtain an acrylic acid-containing solution of high concentration while the acrylic acid loss is decreased. When the whole amount of the discharged gas from the absorption column is cooled and even the amount of the water component discarded to the out side of system is consequently decreased, the absorption ratio of acrylic acid is not enhanced but degraded far more than when the cooling is omitted. Thus, the part of the discharged gas of the acrylic acid absorption column which is recycled to the reactor, namely the so-called recycle gas, alone is cooled so as to induce condensation of the water component and enhance the absorption ratio of acrylic acid. The cooling of the recycle gas results in inducing condensation of not merely the water component but also the acid component, effecting a decrease in the amount of the aid component supplied to the reactor, and eventually preventing the catalyst from being deteriorated by the acid. The condensate produced by this cooling may be returned to the absorption column or discharged to the out side of system instead of being so returned. Though the ratio of acrylic acid loss is not varied very much between these two choices, the return of the condensate to the absorption column is at an advantage in obviating the necessity for the disposal of the waste liquid.

The decrease of the amount of the water component introduced into the system may be accomplished by a method which comprises removing the water component contained in the molecular oxygen-containing gas to be supplied to the reactor and thereafter advancing the gas to the reactor.

In this invention, propylene and/or acrolein can be used as the raw material gas of acrylic acid. While the reactor 20 does not need to be particularly restricted but is only required to be capable of performing a reaction of catalytic gas phase oxidation. The shell-and-tube type reactor can be used advantageously in respect that it excels in the efficiency of reaction. By packing the reactor 20 with the well-known catalyst 10 for catalytic gas phase oxidation and then bringing the raw material gas into contact with such a molecular oxygen-containing gas as oxygen or air, it is made possible to effect the oxidation of the raw material gas. When propylene is used as the raw material gas, the propylene concentration is in the range of 7–15 vol % and the molecular oxygen concentration is such that the ratio of propylene: molecular oxygen (by volume) falls in the range of 1:1.0–2.0. Air may be used as the source of supply of molecular oxygen. When the air contains a water component, it is preferred to be dehumidified prior to the supply thereof to the reactor. The dehumidification is preferred because it is capable of decreasing the amount of water introduced into the reactor and consequently decreasing the amount of water introduced to the absorption column. It is permissible to use an oxygen-enriched air or purified oxygen in the place of air. As concrete examples of the diluting gas 5, nitrogen, carbon dioxide, and other inert gases may be cited.

In this invention, the recycle gas may be introduced into the reactor after it has been cooled to induce condensation of a condensable substance. When the recycle gas is used in this manner, the recycle gas is deprived of the water component in advance so that the water concentration in the raw material gas supplied to the reactor falls in the range of 0–10 vol %, preferably in the range of 0–7 vol %, and particularly in the range of 0–6 vol %. If the concentration exceeds 10 vol %, the excess will possibly result in causing the water component supplied via the reactor to the absorption column to increase the ratio of acrylic acid loss. The total acid concentration is so adjusted at to fall in the range of 0–0.2 vol % and more preferably in the range of 0–0.1 vol %. If the total acid concentration exceeds 0.2 vol %, the excess will possibly result in accelerating the deterioration of the catalyst by oxidation. The recycle gas contains unaltered propylene and acrolien, oxygen, diluting gas, etc. in addition to the water component and the acid component. The propylene, oxygen, water component concentration, and total acid concentration mentioned above can be easily adjusted by computing the amount of the water component contained in the recycle gas and the amount thereof to be incorporated in the raw material gas so as to enable the water component concentration and the total acid concentration in the raw material gas to fall in the optimum ranges mentioned above and computing the propylene concentration and the oxygen concentration in the recycle gas thereby deciding the amount of propylene and the amount of air to be newly supplied to the reactor. The term "total acid" as used herein refers to compounds having a carboxyl group. The recycle gas contains acrylic acid, formic acid, and acetic acid as compounds answering the description.

The reaction of catalytic gas phase oxidation performed by using propylene as the raw material is generally carried out in two stages by the use of two kinds of catalyst 10 for catalytic gas phase oxidation. The catalyst for the first stage of this reaction is capable of forming acrolein mainly by the gas phase oxidation of the raw material gas containing propylene in a gas phase and the catalyst for the second stage of the reaction is capable of forming acrylic acid mainly by the gas phase oxidation of the raw material containing acrolein. As the catalyst for the first stage of the reaction, a complex oxide containing iron, molybdenum, and bismuth may be cited. As the catalyst for the second stage of the reaction, a catalyst having vanadium as an essential component may be cited.

The FIGURE depicts the mode of performing the two-stage reaction mentioned above with a single reactor. Optionally, these reactions may be performed in a tandem system having two different reactors connected to each other. The acrylic acid-containing gas 25 which is obtained by the reaction of catalytic gas phase oxidation contains 5–14 vol % of acrylic acid, 0.1–2.5 vol % of acetic acid, 0.5–3 vol % of molecular oxygen, and 5–36 vol % of water and other components which are by-products of reaction such as the unaltered component of the raw material gas, propionic acid, maleic acid, acetone, acrolein, furfural, formaldehyde and $CO_x$.

In the acrylic acid absorption column 30, any of the known methods of contact may be used for establishing contact between the acrylic acid-containing gas and the absorbing aqueous solution. As concrete examples of such methods of contact, crossflow contact devices using a bubble-cap tray, a uniflat tray, a perforated tray, a jet tray, a valve tray, and a venturi tray; and counter current contact devices using a turbo-grid tray, a dual flow tray, a ripple tray, Kittel tray, gauze type, sheet type, and grid type structured packings and random packings may be cited.

As the absorbing aqueous solution 33 to be used in this invention, a wide variety of aqueous solutions which are capable of absorbing acrylic acid are available. The condensate resulting from cooling the recycle gas may be used as the absorbing aqueous solution. Since the condensate often contains acrylic acid, it is preferred to be reused as the absorbing aqueous solution. The temperature of the absorbing aqueous solution at the time of introduction falls in the range of 0–50° C. and preferably in the range of 10–40° C.

The flow rate ratio of mass of the absorbing water (which excludes the condensate from the recycle gas and corresponds to the absorbing water 33' shown in The FIGURE) to the acrylic acid-containing gas may be properly selected to suit the target acrylic acid concentration. The absorption of acrylic acid is effected by counter current contact using a mass flow rate of the absorbing water of 0.1–1.5 times, preferably 0.1–1.0 times, and particularly 0.15–0.8 times to the mass flow rate of acrylic acid contained in the acrylic acid-containing gas. If the mass flow rate ratio falls short of the level of 0.1 times, the shortage will possibly induce an extreme decrease of the efficiency of the acrylic acid absorption column. Conversely, if it exceeds the level of 1.5 times, the excess will render the acquisition of an acrylic acid-containing solution of high concentration difficult. Incidentally, the absorbing water may contain therein for the purpose of preventing such polymerizing substances as acrylic acid from succumbing to polymerization one or more compounds selected from the group consisting of N-oxyl compounds, phenol compounds, manganese salts such as manganese acetate, copper salts of dialkyl-dithiocarbamic acid such as copper dibutylthiocarbamate, nitroso compounds, amine compounds, and phenothiazine which are cited as in JP-A-2001-348360, 2001-348358, and 2001-348359.

The acrylic acid absorption column is generally operated above normal pressure. In this invention, the column top pressure (gauge pressure) is set in the range of 0–0.4 MPa, preferably in the range of 0–0.1 MPa, and particularly in the range of 0–0.03 MPa. If this pressure falls short of 0 MPa (gauge pressure), the shortage will necessitate a pressure decreasing device and consequently add to the cost of equipment and the cost of utilities. Conversely, if the pressure exceeds 0.4 MPa (gauge pressure), the excess will possibly require the temperature of the absorption column to be elevated considerably for the purpose of discharging a low boiling substance from the column top and consequently degrade absorption efficiency. The column top temperature falls generally in the range of 30–85° C. and particularly in the range of 40–80° C. In this invention, the acrylic acid-containing solution 35 comprising 80–98 wt. % of acrylic acid, 1–19 wt. % of water, and 1–10 wt. % of impurities (such as acids like acetic acid, maleic acid, and propionic acid, and aldehydes like furfural formaldehyde) is obtained under the conditions of absorption mentioned above.

The method for cooling the recycle gas does not need to be particularly restricted. It is only required to resort to a device which is capable of condensing the condensable substances contained in the recycle gas. As concrete examples of the device answering the description, the shell-and-tube type heat exchanger, fin tube type heat exchanger, air cooled heat exchanger, double pipe heat exchanger, coil type heat exchanger, direct contact type heat exchanger, and plate type heat exchanger maybe cited. Since the condensate more often than not contains such polymerizable substances as acrylic acid, however, the method of cooling which resorts to the combination of the cooling column 36 and such a cooling device 39 as illustrated in the FIGURE is commendable in respect that it permits easy supply of a polymerization inhibitor.

The cooling temperature of the recycle gas does not need to be particularly restricted. When the recycle gas is cooled condensation, the concentration of the water component therein falls in the range of 0–10 vol %, preferably in the range of 0–7 vol %, and particularly in the range of 0–6 vol % and further the concentration of the total acid falls in the range of 0–0.2 vol %, preferably in the range of 0–0.1 vol % based on the total amount of the raw material gas supplied to the reactor. When air is used as the molecular oxygen-containing gas, the air contains a water component. The amount of the water component which exists after the recycle gas is cooled is computed from the amount of the air supplied, the aforementioned preferred concentration of the water component in the raw material gas and the amount of the raw material gas supplied. The cooling of Recycle gas is carried out till the concentration the water component reach the value found by the computation. In this invention, the recycle gas is cooled to a temperature which is 1–50° C., preferably 2–40° C., and particularly preferably 3–30° C. lower than the temperature of the waste gas.

Consequently, the bottom liquid of the absorption column having an extremely high acrylic acid concentration is not less than 80 wt. % can be obtained.

(2) Separation of Acrolein

The acrylic acid-containing solution 35 possibly contains acrolein which is the raw material of acrylic acid. For the purpose of removing the contained acrolein, the solution may be supplied to the acrolein separation column 31 and subjected to a treatment for the separation of acrolein.

The separation column does not need to be particularly discriminated but is only required to be capable of separating acrolein. A packed column, a plate column (tray column), etc. are available for the separation. The separation column may be properly selected between the methods of distillation and stripping, depending on the concentration of acrylic acid and the concentration of acrolein in the solution. In the case of distillation, it is advisable to set the column top pressure (absolute value) in a range of 20–800 hPa, preferably in the range of 40–600 hPa, and particularly in the range of 60–400 hPa. If this pressure falls short of 20 hPa (absolute pressure), the shortage will be at a disadvantage in requiring the column, condenser, and vacuum device to be enlarged and consequently necessitating an expense of equipment. Conversely, if the pressure exceeds 800 hPa (absolute pressure), the excess will be at a disadvantage in heightening the temperature inside the separation column and consequently adding to the possibility of polymerization. The column top temperature falls generally in the range of 30–100° C. and particularly in the range of 40–80° C. The column bottom temperature falls generally in the range of 40–110° C. and particularly in the range of 50–90° C. Even in the case of stripping, the separation of acrolein can be attained by any of the hitherto well-known methods. By using these conditions of separation, it is made possible to decrease the amount of acrolein and consequently obtain an acrylic acid-containing solution 35' having an acrylic acid concentration even not less than 80 wt. %.

(3) Distillation of Acrylic Acid-Containing Solution

The acrylic acid-containing solution 35 or 35' is supplied to the first distillation column 40, which discharges a high boiling substance via the bottom thereof and a low boiling substance via the top thereof and separates crude acrylic acid substantially destitute of water as a column bottom stream and/or a column side stream. The first distillation column 40 does not need to be particularly restricted but is only required to be capable of recovering crude acrylic acid. A packed column, a plate column (tray column), etc. for example, are available for the recovery.

In this invention, crude acrylic acid is obtained as a column bottom stream and/or column side stream. Such distillation condition is operated so that low boiling substance such as water and acetic acid can be separated, it may be selected depending on the concentration of acrylic acid in the acrylic acid-containing solution 35 to be introduced and the purity of the crude acrylic acid aimed at. Commendably, the column top pressure (absolute pressure) is set in the range of 20–400 hPa, preferably in the range of 30 hPa–300 hPa, and particularly in the range of 30–200 hPa. If this pressure falls short of 20 hPa (absolute pressure), the shortage will be at a disadvantage in requiring the column, condenser, and vacuum device to be enlarged and the cost of equipment to be unduly increased. Conversely, if the pressure exceeds 400 hPa (absolute pressure), the excess will be at a disadvantage in heightening the temperature inside the distillation column 40 and adding to the possibility of polymerization. The column top temperature falls generally in the range of 30–70° C. and particularly in the range of 40–60° C. Then, the column bottom temperature falls generally in the range of 70–120° C. and particularly in the range of 80–110° C. The distillation performed under these conditions produces crude acrylic acid containing substantially no water and having an acetic acid content in the range of 0–1.0 wt. % as a column bottom stream and/or a column side stream of the distillation column.

During the distillation, a polymerization inhibitor may be added to the reflux liquid for the purpose of preventing such polymerizable substances as acrylic acid from succumbing to polymerization. As the polymerization inhibitor, the aforementioned various polymerization inhibitors which can be added to the absorbing water may be adopted.

When the column side stream is withdrawn in a vaporous form, part of such high boiling substances as polymerization inhibitor and substance causing coloration which are generated within the column can be removed. Thus, high purified acrylic acid can be obtained by performing the step of crystallization up to several repetitions. Specifically, since the reflux liquid flows from the top toward the bottom of the column, a liquid collecting device disposed inside the distillation column is capable of withdrawing the column side stream in a liquid form. The polymerization inhibitor which has been added to the distillation column, however, has a high boiling point and cannot exist in a vaporous form in the distillation column and persists as dissolved in the liquid phase inside the column. When the column side stream is withdrawn in a liquid state, therefore, the withdrawn liquid inevitably entrains such involatile component such as polymerization inhibitor. When the column side stream is withdrawn in the vaporous form, however, acrylic acid can be obtained in a state deprived of such nonvolatile substances as polymerization inhibitor.

For the sake of enabling the distillation column to withdraw the column side stream in the vaporous form while accomplishing the inherent object of distillation, the pressures in the column side part and the column top part are required to be so controlled as to satisfy this relation, pressure in the column bottom part>pressure in the column side part>pressure in the column top part. If the pressure in the column top part and the pressure in the column side part are equal, the essential distillation which resides in separating a target component by virtue of the difference of boiling points will not be fulfilled because the whole amount of the vapor is withdrawn from the column side part. To be specific, control the pressure of the column top part to the value suited for distillation by use of a vacuum device (not shown) and then the pressure of the column side part is made to surpass the pressure of the column top part with the same vacuum device. By setting these differences of pressure, it is made possible to withdraw the column side stream in the vaporous form from the column side part. Incidentally, the pressure of the column side part relative to the pressure of the column top part may be properly selected, depending on the amount of the column side stream, the position of withdrawing in the column side part, and the amount of impurities to be contained. The proper difference between the pressure in the column top part and the pressure in the column side part may be set by performing the distillation under the pressure of the column side part which is made in advance to surpass the pressure of the column top part and then controlling the relevant pressures based on the composition of the produced column side stream and the amount of distillation.

In this invention, the term "column side stream" means the flow drawn from the column side part of the distillation column and the term "column side part" means the position excluding the column top part and the column bottom part. The position for withdrawing the column side stream, therefore, may be properly selected anywhere in the column side part, depending on the target substance for distillation and the conditions of distillation. For the purpose of efficiently removing the involatile component in the plate column, for example, it is appropriate to have a withdrawing port disposed above the pertinent plate in the column so as to allow only the vaporous substance to be withdrawn but not allow the liquid on the plate to be withdrawn.

This invention is characterized by obviating the necessity of using an azeotropic solvent. Since the acrylic acid-containing solution of high concentration can be prepared at the step of absorption, such low boiling substances as water and acetic acid which are contained in the solution can be efficiently separated as the column top distillate of the first distillation column 40 without requiring use of an azeotropic solvent. Further, the use of an azeotropic solvent possibly results in inducing oil-water separation in the distillation column during the azeotropic dehydration and hindering the effect of preventing polymerization because of the local presence of the polymerization inhibitor in the water phase or the oil phase. The stability of polymerization in the distillation column, therefore, is effectively derived from no use of an azeotropic solvent. The absence of the use of an azeotropic solvent is also at an advantage in permitting the distillate to be used as an acetic acid-containing aqueous solution without entailing oil-water separation. It has been found that the azeotropic distillation becomes substantially infeasible when the acrylic acid concentration in the acrylic acid-containing solution exceeds 80 wt. %. If an azeotropic solvent is used during the distillation of the acrylic acid-containing solution of such high concentration, the separation between the oil phase (azeotropic solvent phase) and the water phase will become difficult owing to the high acrylic acid concentration in the distillate. Even if this separation is attained, the water phase will have the azeotropic solvent dissolved therein in a large amount. When the water phase containing acrylic acid is directly circulated to the absorption column, therefore, the azeotropic solvent is circulated also to the reactor and consequently suffered to deteriorate the catalyst and curtail the service life of the catalyst. On the other hand, if the acrylic acid concentration on the distillate is lowered, the crude acrylic acid is consequently compelled to contain the azeotropic solvent in a large amount, it becomes difficult to obtain the crude acrylic acid having purity enough for a finished product even by performing the crystallization up to several repetitions.

When the distillation is performed with no use to azeotropic distillation as contemplated by this invention, azeotropy occurs between the acrylic acid and water, induces distillation of a considerable amount of acrylic acid from the column top part of the distillation column, and entails acrylic acid loss. In this invention, therefore, it is appropriate to circulate the distillate of the distillation column to the absorption column to recover the acrylic acid contained in distillate in the absorption column.

The position at which the column top liquid of the first distillation column circulated toward the absorption column enters the absorption column does not need to be particularly restricted but is only required to be different from the top of the absorption column. The term "different from the column top" refers to a number of theoretical plate in the range of 2–100 as counted on the assumption that the number of theoretical plate 1 represents the top of the distillation column and the number of theoretical plate 100 represents the bottom thereof. The top liquid of the first distillation column contains such low boiling substances as water and acetic acid. In the absorption column, acrylic acid is absorbed by the absorbing aqueous solution 33 which falls from the top of the column. In this case, the absorption ratio of acrylic acid is enhanced by introducing acetic acid via any of the positions excluding the top of the absorption column. Though the mechanism responsible for this enhancement of the absorption ratio remains yet to be clarified, it may be logically explained by a supposition that when the acetic acid is introduced via any of the positions of the absorption column 30, a layer of acetic acid gas is formed in the neighborhood of the position for supply of the acetic acid and the gas distribution in the absorption column is so changed as to form a low boiling substance gas layer above the acetic acid layer and a high boiling substance as layer under the acetic acid layer and, as a result, acrylic acid migrates toward the column bottom. This invention, by circulating the column top liquid of the first distillation column to the absorption column, is enabled to attain recovery of acrylic acid and as well enhance the absorption ratio of acrylic acid by dint of the acetic acid contained in the solution. The position forming the destination of the circulation of the liquid to the absorption column is properly selected so that the acetic acid-containing solution is introduced below the intermediate stage of the absorption column, specifically in the range of number of theoretical plates 2–100, preferably 25–100, and particularly 50–100. At the column top, the formation of the acetic acid gas layer no longer produces an effect of enhancing the absorption efficiency of acrylic acid but rather results in lowering the concentration of acrylic acid on the column bottom side owing to a decrease of the absorption ratio of acrylic acid and renders the acquisition of an acrylic acid-containing solution of high concentration impossible. Particularly, the amount of acetic acid to be introduced is set at a mass flow rate 0.005–0.20 times, preferably 0.008–0.15 times, and particularly 0.01–0.10 times the mass flow rate of acrylic acid contained in the acrylic acid-containing gas. If the mass flow rate falls short of 0.005 times, the shortage will result in dulling the effect of enhancing the absorption efficiency of acrylic acid. Conversely, the mass flow rate exceeds 0.20 times, the excess will result in rendering the acquisition of an acrylic acid-containing solution of high concentration difficult.

This invention, by circulating the distillate to the absorption column, is enabled to repress the acrylic acid loss to the same level as is attained when an azeotropic solvent is used.

(4) Step of Crystallization of Crude Acrylic Acid

This invention supplies the crude acrylic acid 41 to the crystallizing device 50 to obtain acrylic acid 60 as a finished product. The method of crystallization to be used does not need to be particularly restricted but is required to effect the crystallization either continuously or batchwise. It is allowed to execute the crystallization in one stage or in two or more stages. As a concrete example of the continuous crystallizing device, backmixing column crystallizer (BMC) (made by Nippon Steel Chemical Co., Ltd.) as a column type crystallizer having a crystallizing part, a solid-liquid separating part, and a crystal purifying part integrated may be cited. A cooling disk crystallizer (CDC) (made by Gouda Company of Netherlands), for example, is used as the crystallizing part, a belt filter or a centrifugal separator, for example, is used as the solid-liquid separating part, and Kureha Crystal Purifier (KCP) (made by Kureha TechnoEngineering Co. Ltd.), for example, is used as the crystal purifying part respectively in the continuous crystallizing device.

As concrete examples of the batchwise crystallizing device, a layer crystallizing device (dynamic crystallizing device) made by Sulzer Chemtech Company of Switzerland and a static crystallizing device made by BEFS PROKEM Company of France may be cited.

The method of multistage fractional crystallization forms one of the advantageous modes of embodying this invention. This method properly performs the crystallization by a step of dynamic crystallization using a dynamic crystallizing device provided with a tubular crystallizing device provided with a temperature controlling mechanism for performing crystallization, sweating, and melting, a tank for recovering the mother liquid occurring after the sweating, and a circulating pump for supplying acrylic acid to the crystallizing device and adapted to transfer acrylic acid by means of a circulating pump from a storage vessel disposed in the lower part of the crystallizing device to the upper part of the tube of the crystallizing device or by the combination of a step of dynamic crystallization and a step of static crystallization using a tubular crystallizing device provided with a temperature controlling mechanism for performing crystallization, sweating, and melting and furnished in the lower part thereof with an drawing-out valve and using a tank for recovering the mother liquid occurring after the sweating with a step of static crystallization.

The crude acrylic acid in the liquid phase is introducefd into the crystallizing device. Then, the solid phase differing in composition from the introduced liquid phase is solidified in the cooling surface. After 40–90 wt. %, preferably 50–80 wt. % of the used acrylic acid is solidified, the remainder of the liquid phase is immediately separated and removed. This separation and removal is effected by scooping out the residual phase with a pump (step of dynamic crystallization) or causing it to flow out (step of static crystallization). It may be further followed by a step of washing the crystal layer or a step of sweating, namely partial melting of an impure crystal region.

When the dynamic crystallization and the static crystallization are carried out by a multistage process, they can be advantageously executed by the principle of counter current, the substances crystallized in the component processes are separated from the respective residual mother liquids after crystallization, these crystallized substances are supplied to respective pertinent steps involving still higher levels of purity, and the residues of crystallization are supplied to respective pertinent steps involving still lower levels of purity.

Generally, all the steps in which acids of higher levels of purity than the supplied crude acid solutions are known as purifying steps and all the other steps are known as stripping steps. The stripping steps are executed for the purpose of recovering acrylic acid in the mother liquid from the relevant purifying steps. The dynamic crystallization attains crystallization with difficulty which increases in accordance as the purity of acrylic acid decreases. In contrast, the static crystallization attains crystallization easily even when the purity of acrylic acid decreases as compared with the dynamic crystallization. For the purpose of exalting the ratio of recovery of acrylic acid, therefore, the final mother liquid of the dynamic crystallization is further crystallized by the static crystallization.

The number of steps of crystallization to be required depends on the degree of purity to be demanded. For the purpose of producing acrylic acid of high purity, it is proper to perform 1–5, preferably 2–3 purifying steps (dynamic crystallizing steps), 1–5, preferably 1–4 stripping steps (dynamic crystallizing steps), and 1–5, preferably 1–3 stripping steps (static crystallizing steps).

(5) Decomposition of Acrylic Acid Dimer

In this invention, it is proper to use as a device for decomposing acrylic acid dimer the combination of the distillation column 70 provided on the bottom side thereof with the thin layer evaporator 73 and the dimer decomposing tank 75 for heating the bottom liquid of the vaporizing device 73 illustrated in The FIGURE. It is advisable to have the thin layer evaporator 73 disposed on the column bottom side because the bottom liquid of the second distillation column 70 have high viscosity. The second distillation column 70 is preferred to effect the distillation in a number of theoretical plate in the range of 1–5, under a reduced pressure in the range of 10–150 hPa (absolute pressure), at a column bottom temperature of not higher than 120° C. Incidentally, the high boiling substances contained in the bottom liquid of the first distillation column 40 include acrylic acid dimer, maleic acid, and polymerization inhibitor, for example.

Then, the bottom liquid of the thin layer evaporator 73 mentioned above is supplied to the dimer decomposing tank 75. This dimer decomposing tank 75 decomposes acrylic acid dimer at a temperature in the range of 120–220° C. The hold up time (capacity of dimer decomposing tank/amount of waste oil) varies with the temperature of thermal decomposition. It generally falls in the range of 0.1–60 hours. Preferably, it is in the range of 5–50 hours and particularly in the range of 20–30 hours. The dimer decomposing tank, during decomposing the acrylic acid dimer, allows addition thereto such catalysts for decomposition as an alkali metal salt, an alkaline earth metal salt, and an N-oxyl compound described in JP-A-2003-89672. Particularly, the use of the N-oxyl compound mentioned above as a polymerization inhibitor at the step of absorption or the step of distillation is advantageous in respect that it can additionally play as a catalyst for decomposition of the acrylic acid dimer.

After the acrylic acid dimer has been decomposed into acrylic acid, this acrylic acid can be effectively recovered by supplying the product of decomposition to the thin layer evaporator 73 and the distillate from the top of the second distillation column to the first distillation column 40. This invention contemplates preparing an acrylic acid-containing solution of high concentration in the acrylic acid absorption column 30 and preventing the acrylic acid-containing solution of high concentration from polymerization by the addition of a polymerization inhibitor. At the step of absorption and the step of purification, the polymerization inhibitor is used in amounts proportional to the concentrations of acrylic acid. Since the polymerization inhibitor is expelled to the out side of system as the waste liquid of the dimer decomposing tank 75, the acrylic acid 60 produced as a finished product enjoys high purity.

Incidentally, in this invention, acrylic acid may be distilled out of the top of the second distillation column 70, circulated to the absorption column 30 and the first distillation column 40, and consequently recovered as crude acrylic acid.

The residual mother liquid recovered from the crystallizing device 50 may be supplied in its whole amount to any of the absorption column 30, the first distillation column 40, the second distillation column 70, the thin layer evaporator 73, and the dimer decomposing tank 75. It may be partly expelled to the out side of system as waste oil. When the whole amount of the residual mother liquid is supplied to the step of decomposing the acrylic acid dimer, part of the acrylic acid which is recovered from the step of decomposing the acrylic acid dimer may be discharged out of the system for the purpose of avoiding concentration of an impurity. Otherwise, the residual mother liquid may be subjected to a chemical pretreatment for transforming aldehydes and maleic acid into high boiling substances before it is subjected to the step of decomposing the acrylic acid dimer. As a result, the acrylic acid recovered by the step of decomposing the acrylic acid dimer is enabled to lower the impurity concentration thereof. This operation may be carried out by following the procedure taught in JP-A-2001-199931.

EXAMPLES

Now, this invention will be described more specifically below with reference to working examples cited herein below.

(Example of Production of Catalyst)

A molybdenum-bismuth type catalyst was prepared by following the procedure of Example 1 cited in JP-A-2000-325795. It is labeled as "catalyst (I)." A molybdenum-vanadium type catalyst was prepared by following the procedure of Example 1 cited in JP-A-1996-206504. It was labeled as "catalyst (II)."

Example 1

Acrylic acid was produced by using an apparatus illustrated in The FIGURE.

A reactor furnished on the outer periphery thereof with a jacket for circulating a heat medium, containing therein reaction tubes 25 mm in inside diameter and 7,000 mm in length, and provided at a position of 3,500 mm from the lower part of the jacket with a perforated tube sheet dividing the heat medium jacket into two halves, an upper one and a lower one, was used. The lower part (the first reaction zone) and the upper part (the second reaction zone) of the reactor had their temperatures controlled by circulation of their respective heat media. The reactor was packed with (1) ceramic balls having an average diameter of 5 mm, (2) a mixture of catalyst (I) and ceramic balls of an average diameter of 5 mm at a volume ratio of 70:30, (3) catalyst (I), (4) raschig rings made of stainless steel and measuring 5 mm in outside diameter, 4.5 mm in inside diameter, and 6 mm in length, (5) a mixture of catalyst (II) and ceramic balls of an average diameter of 5 mm at a volume ratio of 75:25, and (6) catalyst (II) placed sequentially from the lower part toward the upper part of the reactor in respective bed lengths of 250 mm, 700 mm, 2,300 mm, 500 mm, 600 mm, and 1,900 mm.

To the first reaction zone of the reactor, propylene, air (the concentration of water component 2 wt. %), and part of the discharged gas (recycle gas) from the absorption column were circulated to supply 8.0 vol % of propylene, 14.4 vol % of $O_2$, and 2.0 vol % of $H_2O$ (the remainder comprising $N_2$, propane, COx, acrylic acid, and acetic acid) with the respective flow rates and the cooling temperature of the recycle gas so adjusted as to set the space velocity in the first reaction zone at 1,250 $hr^{-1}$ (STP).

The heat medium temperatures of the first reaction zone and the second reaction zone were so adjusted as to set the degree of conversion of propylene at 97±0.5 mol % and the yield of acrolein at 1±0.5 mol % under the outlet pressure, 0.15 MPa (absolute pressure), of the second reaction zone to obtain an acrylic acid-containing gas having an acrylic acid concentration of 16.62 wt. % at a rate of 26.74 kg/hour.

The acrylic acid-containing gas thus obtained was cooled to 170° C. with a precooler and then led to an acrylic acid absorption column so as to be absorbed therein in the form of an acrylic acid-containing solution.

The absorption column was a packed column filled with structured packings and furnished with a number of theoretical plate 21 found by computation. It was provided in the column bottom part with a supply port for an acrylic acid-containing gas and withdrawing port for the absorbed liquid, in the column top part with an inlet port for the absorbing aqueous solution and a discharge port for the gas, and in the column side part (the $19^{th}$ theoretical plate) with a supply tube for the column top liquid from the distilling tower and further provided with a cooling device for cooling part of the gas emanating from the column top.

As the absorbing water, water containing hydroquinone in an amount corresponding to 200 wt. ppm relative to the amount of the acrylic acid in the acrylic acid-containing gas introduced into the absorption column was supplied at a rate of 1.16 kg/hour.

The acrylic acid absorption column was operated, with the column top temperature set at 65.1° C., the column top pressure at 0.11 MPa (absolute pressure), the cooling temperature of the recycle gas at 40.6° C., and the ratio of recycling at 29.0%.

Via the column side part, the column top liquid of the distillation column having a composition of 58.3 wt. % of acrylic acid, 21.7 wt. % of $H_2O$, and 20.0 wt. % of acetic acid was supplied at a rate of 1.00 kg/hour.

Further, this acrylic acid-containing solution was supplied to the upper part of the packed column measuring 100 mm in inside diameter and 5 m in packed height. The packed column was operated under a column top pressure of 265 hPa (absolute pressure) at a column bottom temperature of 70° C. kept by heating so as to effect distillation and separation of acrolein and the like. As a result, an acrylic acid-containing solution containing 90.0 wt. % of acrylic acid, 4.0 wt. % of water, 3.9 wt. % of acetic acid, and 2.1 wt. % of other components (such as acids like maleic acid and propionic acid and aldehydes like furfural, formaldehyde, benzaldehyde, and glyoxal) was obtained via the column bottom part at a rate of 5.50 kg/hour. Incidentally, the gas obtained via the column top part was supplied to the lower parat of the acrylic acid absorption column.

Then, the acrylic acid-containing solution was distilled in the distillation column. This distillation column was equipped with dual flow trays having 60 plats and a distance of 147 mm between the plates, provided in the column top part with a distilling tube, in the central part with a raw material supply tube, and in the column bottom part with a bottom liquid withdrawing tube, below the raw material supply tube with a gaseous acrylic acid withdrawing tube for which acrylic acid is withdrawn in the gas state, and further provided at the $57^{th}$ plate from the column top with a condenser for cooling the acrylic acid gas.

The operation of distillation was carried out, with the column top pressure decompressed by a vacuum device (not shown) so as to set the working pressure thereof at 100 hPa (absolute pressure), the pressure difference between the column side part and the column top part controlled at 99 hPa so as to set the flow rate ratio of the gaseous acrylic acid and the distillate from the column top part at 4:1, and the reflux ration was 3.4. 4H-TEMPO (4-hydroxy-2,2,6,6-tetramethyl piperidinoxyl) added as a stabilizer from the reflux line in an amount corresponding to 200 ppm relative to the acrylic acid supplied.

Via the gaseous acrylic acid withdrawing tube, crude acrylic acid containing 99.4 wt. % of acrylic acid, 0.3 wt. % of acetic acid, 0.002 wt. % of acrylic acid dimer and 0.3 wt. % of other components was obtained at a rate of 4.33 kg/hour.

The acrylic acid-containing solution obtained from the column top part and having a composition of 58.3 wt. %, 21.7 wt. % of $H_2O$, and 20.0 wt. % of acetic acid was circulated to the column side part of an acrylic acid absorption column.

The bottom liquid obtained from the column bottom part and containing 48.7 wt. % of acrylic acid and 30.2 wt. % of acrylic acid dimer was supplied to the intermediate part of the distillation column of the acrylic acid dimer decomposing device.

At this time, an aqueous 20 wt. % sodium oxide solution which was a catalyst for the decomposition of acrylic acid dimer was added in an amount of 0.04 wt. % (as reduced to NaOH) to the acrylic acid-containing solution to be supplied.

The device for the decomposition of acrylic acid dimer was composed of a distillation column furnished with 15 dual flow trays, a thin layer evaporator, and a dimer decomposing tank and was capable of effecting thermal decomposition under the conditions of 140° C. of internal temperature of the dimer decomposing tank and 30 hours of hold up time. It was operated under the conditions of 33 hPa of column top pressure and 0.9 of reflux ratio while the thin layer evaporator was controlled so as to set the column bottom temperature at 85° C. An acrylic acid having an acrylic acid content of 99.4 wt. % was recovered via the column top part and circulated to the column bottom part of the distillation column. At this time, the yield of purification of crude acrylic acid was 97.0 wt. %.

Then, the crude acrylic acid was supplied to a crystallizing unit and purified therein by performing a step of dynamic crystallization twice. Further, the residue of crystallization at the purifying step was treated by performing a step of dynamic crystallization three times and a step of static crystallization twice.

The dynamic crystallization was performed by following the procedure adopted for the operation of a crystallizing device disclosed in JP-B-1978-41637. To be specific, this device was a metal tube provided in the lower part with a storage vessel and measuring 6 m in length and 70 mm in inside diameter and was adapted to transfer the liquid in the storage vessel with a circulating pump to the upper part of the tube and allow the liquid to fall down the inner wall surface of the tube in the form of a film (falling film). The surface of this tube was formed of a double-wall jacket. The jacket functioned as a thermostat and controlled so as to be set at a stated temperature. One dynamic crystallization was performed by the following procedure.

1. Crystallization: Acrylic acid was supplied to the storage vessel, caused by the circulating pump to fall down the wall surface of the tube in the form of a film, and cooled by lowering the temperature of the jackets below the solidification point so as to crystallize about 60–80 wt. % thereof on the wall surface of the tube.

2. Sweating: The circulation pump was stopped, the jacket temperature was increased to the vicinity of the freezing point, and the acrylic acid is caused to sweat about 2–5 wt % thereof. After sweating, the residual melt is pumped out.

3. Melting: The crystals were melted by elevating the temperature of the jacket beyond the solidification point and the melt was scooped out with the pump.

In the foregoing operation, the temperatures and the solidification points were made to depend on the relevant steps performed.

The device for the static crystallization was a tube provided in the lower part with an drawing-out valve and measuring 90 mm in inside diameter and 1 m in length. The surface of this tube was formed of a double-wall jacket, which was adapted to serve as a thermostat and was controlled so as to be set at a certain fixed temperature. One static crystallization was performed by the following procedure.

1. Crystallization: Acrylic acid was supplied into the tube and crystallized therein by lowering the temperature of the jacket to below the solidification point so as to have about 60–80 wt. % thereof crystallized.

2. Sweating: The residual mother liquid occurring after the crystallization was withdrawn from the lower part of the tube and deprived of about 15–25 wt. % thereof by sweating, with the temperature of the jacket elevated to the neighborhood of the solidification point. After the sweating, the liquid formed by the sweating was withdrawn.

3. Melting: The crystals were melted by elevating the temperature of the jacket beyond the solidification point and the resultant melt was withdrawn.

As a result, acrylic acid having such a high purity as 99.94 wt. % was obtained at a rate of 4.25 kg/hour.

The acrylic acid contained 467 wt. ppm of acetic acid, 88 wt. ppm of propionic acid, 0.5 wt. ppm of furfural, and 0.6 wt. ppm of benzaldehyde.

Comparative Example 1

The acrylic acid-containing solution obtained in Example 1 and containing 90.0 wt. % of acrylic acid, 4.0 wt. % of water. 3.9 wt. % of acetic acid, and 2.1 wt. % of other components (such as acids like maleic acid and propionic acid and aldehydes like furfural, formaldehyde, benzaldehyde, and glyoxal) was subjected to azeotropic distillation with toluene used as an azeotropic solvent.

The azeotropic distillation was carried out by using the same device as in Example 1, with the column top pressure set at 75 hPa and the reflux ratio at 9.5.

Crude acrylic acid containing 99.4 wt. % of acrylic acid, 0.30 wt. % of acetic acid, 0.002 wt. % of acrylic acid dimer, and 0.3 wt. % of other component was obtained through the gaseous acrylic acid extracting tube at a rate of 4.30 kg/hour.

From the column top part, a water phase containing 40.8 wt. % of acrylic acid, 24.9 wt. % of acetic acid, 27.0 wt. % of water, and 7.3 wt. % of toluene was obtained at a rate of 0.82 kg/hour. Since this water phase contained toluene in a large amount, it could not be circulated to the absorption column. If the solution was circulated to the absorption column, it would induce supply of toluene to the catalyst system and occur inevitably poison for the catalyst.

The invention claimed is:

1. A method for the production of acrylic acid, comprising the steps of
    a-1) obtaining an acrylic acid-containing gas by catalytic vapor phase oxidation of a raw material of acrylic acid,
    a-2) introducing said acrylic acid-containing gas into an absorption column, so as to allow said gas to contact an absorbing aqueous solution therein, to obtain an aqueous acrylic acid solution having not less than 85% by mass of acrylic acid content,
    a-3) cooling at least a part of a gas discharged from the top of the absorption column, and recycling the cooled gas to a catalytic oxidation reactor, wherein the cooling is in the range of 1–50° C. lower than when discharged from the top of the absorption column,
    a-4) recycling to step (a-2) at least a part of a condensed liquid obtained by cooling said discharged gas,
    b) distilling said acrylic acid-containing solution in the absence of an azeotropic solvent and obtaining crude acrylic acid as a column bottom stream and/or a column side stream, and
    c) supplying said crude acrylic acid to a crystallization step and melt crystallizing said crude acrylic acid and obtaining purified acrylic acid.

2. A method according to claim 1, which further comprises a step of supplying the bottom liquid of the distillation column of said step b) to an acrylic acid dimer decomposing device.

3. A method according to claim 2, which further comprises a step of circulating the distillate from said acrylic acid dimer decomposing device to the absorption column of said step a) and/or the distillation column of said step b).

4. A method according to claim 1, which further comprises a step of circulating the column top liquid of the distillation column of said step b) to the absorption column of said step a-2.

5. A method according to claim 1, wherein the acrylic acid-containing solution obtained at said step a-2 is treated for separation of acrolein contained therein and then the resultant acrylic acid-containing solution is introduced to said step b).

6. A method according to claim 1, wherein the temperature for cooling the gas discharged from the top of the absorption column is in the range of 2–40° C. lower than the temperature of a gas wasted from the top of the absorption column.

7. A method according to claim 1, wherein the water content in the recycled gas is in the range of 0–10 vol. %.

8. A method according to claim 1, wherein the concentration of the total acid is in the range of 0–0.2 vol. %.

9. A method according to claim 5, wherein the pressure of the top of the column is in the range of 20–800 hPa and the temperature is in the range of 30–100° C.

10. A method according to claim 2, wherein the pressure of the top of the distillation column is in the range of 20–400 hPa and temperature is in the range of 30–70° C.

11. A method according to claim 3, wherein the decomposition of said acrylic acid dimer is carried out at a temperature in the range of 120–220° C. and a holdup time is in the range of 0.1–60 hours.

12. A method for the production of acrylic acid, comprising the steps of
    a-1) obtaining an acrylic acid-containing gas by catalytic vapor phase oxidation reaction of a raw material of acrylic acid,
    a-2) introducing said acrylic acid-containing gas into an absorption column, so as to allow said gas to contact an absorbing aqueous solution therein to obtain an aqueous acrylic acid solution having not less than 85% by mass of acrylic acid content, a-3) cooling at least part of a gas discharged from the top of the absorption column, and recycling the gas to a catalytic oxidation reactor, a-4) recycling to said absorption column at least part of a condensed liquid obtained by cooling said discharged gas, b) distilling said acrylic acid-containing solution in the absence of an azeotropic solvent and obtaining crude acrylic acid as a column bottom stream and/or a column side stream, and c) supplying said crude acrylic acid to a crystallization step and melt crystallizing said crude acrylic acid and obtaining purified acrylic acid.

* * * * *